United States Patent
Nishida et al.

(10) Patent No.: US 10,748,733 B2
(45) Date of Patent: Aug. 18, 2020

(54) ION GENERATION DEVICE, METHOD FOR PRODUCING ION GENERATING DEVICE, AND ELECTRICAL DEVICE

(71) Applicant: SHARP KABUSHIKI KAISHA, Sakai, Osaka (JP)

(72) Inventors: Hiromu Nishida, Sakai (JP); Satoshi Okano, Sakai (JP); Nobuyuki Ohe, Sakai (JP); Mitsuyoshi Yamashita, Sakai (JP)

(73) Assignee: SHARP KABUSHIKI KAISHA, Sakai, Osaka (JP)

( * ) Notice: Subject to any disclaimer, the term of this patent is extended or adjusted under 35 U.S.C. 154(b) by 213 days.

(21) Appl. No.: 15/552,482

(22) PCT Filed: Feb. 9, 2016

(86) PCT No.: PCT/JP2016/053833
§ 371 (c)(1),
(2) Date: Aug. 21, 2017

(87) PCT Pub. No.: WO2017/038111
PCT Pub. Date: Mar. 9, 2017

(65) Prior Publication Data
US 2018/0053621 A1 Feb. 22, 2018

(30) Foreign Application Priority Data
Sep. 2, 2015 (JP) .................. 2015-173250

(51) Int. Cl.
*H01J 27/26* (2006.01)
*A61L 9/22* (2006.01)
(Continued)

(52) U.S. Cl.
CPC .............. *H01J 27/26* (2013.01); *A61L 9/22* (2013.01); *B60H 3/0071* (2013.01); *H01J 27/22* (2013.01);
(Continued)

(58) Field of Classification Search
CPC ......... A61L 9/22; B03C 2201/06; B03C 3/38; B03C 3/40; B03C 3/41; B03C 3/74;
(Continued)

(56) References Cited

U.S. PATENT DOCUMENTS 5,958,165 A * 9/1999 Takeuchi ................ B32B 18/00
156/89.11
6,653,638 B2 * 11/2003 Fujii ....................... H01T 23/00
250/324
(Continued)

FOREIGN PATENT DOCUMENTS

| CN | 201478694 U | 5/2010 |
| CN | 204165142 U | 2/2015 |

(Continued)

OTHER PUBLICATIONS

Co-pending letter.
(Continued)

*Primary Examiner* — Jared Fureman
*Assistant Examiner* — Nicolas Bellido
(74) *Attorney, Agent, or Firm* — ScienBiziP, P.C.

(57) ABSTRACT

The present invention has an object to reduce a risk of performance degradation caused to an ion generating device that is being manufactured. An ion generating device (1) includes: a discharge electrode (21) for generating ions by electric discharge, the discharge electrode having (i) a mounting part (33*a*) for mounting the discharge electrode on the ion generating device and (ii) a brush part including a plurality of linear electrically conductive members, and the (Continued)

mounting part (33*a*) binding a base end part of the brush part so as to hold the base end part, the ion generating device further including: an insulating sealing member (41) with which to seal the base end part of the mounting part (33*a*); and a protective resin (29) with which to cover at least a brush base end surface (25*t*).

4 Claims, 6 Drawing Sheets

(51) Int. Cl.
*B60H 3/00* (2006.01)
*H01J 27/22* (2006.01)
*H01T 19/04* (2006.01)
*H01T 19/00* (2006.01)
*H01T 23/00* (2006.01)

(52) U.S. Cl.
CPC ............. *H01T 19/00* (2013.01); *H01T 19/04* (2013.01); *H01T 23/00* (2013.01)

(58) Field of Classification Search
CPC .................. B03C 3/743; B60H 3/0071; B65H 2301/5133; C01B 13/11; C02F 1/4608; F24F 7/00; F24F 2003/1682; F24F 3/166; G03G 15/0291; H01J 27/02; H01J 27/22; H01J 27/26; H01T 19/04; H01T 23/00; H01T 19/00; H01T 19/02; H05F 3/04; H05H 2001/481
USPC ........................................................ 361/231
See application file for complete search history.

(56) References Cited

U.S. PATENT DOCUMENTS

| | | | | |
|---|---|---|---|---|
| 2006/0214111 | A1* | 9/2006 | Luo | H01T 23/00 250/423 R |
| 2009/0042502 | A1 | 2/2009 | Kim et al. | |
| 2010/0175391 | A1 | 7/2010 | Jee et al. | |
| 2011/0250475 | A1* | 10/2011 | Yamamoto | H01M 2/0277 429/7 |
| 2012/0326197 | A1* | 12/2012 | Ohbayashi | C09K 11/025 257/98 |
| 2013/0120895 | A1 | 5/2013 | Lai | |
| 2013/0146781 | A1* | 6/2013 | Sekoguchi | H01T 23/00 250/423 R |
| 2013/0214173 | A1 | 8/2013 | Noda et al. | |
| 2014/0103793 | A1* | 4/2014 | Nishida | H01T 19/04 313/231.71 |
| 2016/0104595 | A1 | 4/2016 | Nishida et al. | |
| 2016/0204581 | A1 | 7/2016 | Nishida et al. | |
| 2016/0218490 | A1* | 7/2016 | Nishida | A61L 9/22 |
| 2018/0053620 | A1* | 2/2018 | Nishida | A61L 9/22 |
| 2018/0053621 | A1* | 2/2018 | Nishida | A61L 9/22 |

FOREIGN PATENT DOCUMENTS

| | | | |
|---|---|---|---|
| CN | 105493361 A | | 4/2016 |
| EP | 0048102 A1 | | 3/1982 |
| JP | H08-112549 A | | 5/1996 |
| JP | 10074576 A | * | 3/1998 |
| JP | 11168276 A | * | 6/1999 |
| JP | 2000-340393 A | | 12/2000 |
| JP | 3089869 U | | 11/2002 |
| JP | 2003-229232 A | | 8/2003 |
| JP | 3112435 U | | 8/2005 |
| JP | 2008-34220 A | | 2/2008 |
| JP | 2008034220 A | * | 2/2008 |
| JP | 2008-101818 A | | 5/2008 |
| JP | 2008101818 A | * | 5/2008 |
| JP | 2008112714 A | * | 5/2008 |
| JP | 2009-238602 A | | 10/2009 |
| JP | 2012-038510 A | | 2/2012 |
| JP | 3174998 U | | 4/2012 |
| JP | 2014-032783 A | | 2/2014 |
| JP | 2015-5387 A | | 1/2015 |
| JP | 2017-021982 A | | 1/2017 |
| KR | 20-0429549 Y1 | | 10/2006 |
| WO | 2014/185682 A1 | | 11/2014 |
| WO | WO-2015050045 A1 | * | 4/2015 ............ H01T 19/04 |

OTHER PUBLICATIONS

Office Action dated Jun. 27, 2019 issued in U.S. Appl. No. 15/552,480.
Office Action dated Oct. 1, 2019 for U.S. Appl. No. 15/552,480.
Office Action dated Mar. 6, 2020 for U.S. Appl. No. 15/552,480.

* cited by examiner

ION GENERATION DEVICE, METHOD FOR PRODUCING ION GENERATING DEVICE, AND ELECTRICAL DEVICE

TECHNICAL FIELD

The present invention relates to an ion generating device, a method for manufacturing the ion generating device, and an electrical apparatus including the ion generating device.

BACKGROUND ART

An ion generating device has been conventionally used for, for example, indoor air cleaning, sterilization, or deodorization.

An ion generating device generally includes a discharge electrode for generating ions by electric discharge. An ion generating device generates ions by, for example, causing corona discharge to occur between (a) a tip of a discharge electrode to which a high voltage is applied and (b) an induction electrode.

As a discharge electrode for generating ions by thus applying thereto a high voltage, a brush-like discharge electrode including a plurality of fibrous electrically conductive members having bundled roots is known.

For example, Patent Literature 1 discloses a brush-like discharge electrode that is arranged such that while a bundle of carbon fibers partially extends out from one end of a metallic pipe by a given length, the metallic pipe is pressure-fixed to the other end of the bundle of carbon fibers.

CITATION LIST

Patent Literatures

[Patent Literature 1]
Japanese Patent Application Publication, Tokukai, No. 2003-229232 (Publication Date: Aug. 15, 2003)
[Patent Literature 2]
Japanese Patent Application Publication, Tokukai, No. 2008-34220 (Publication Date: Feb. 14, 2008)
[Patent Literature 3]
Japanese Patent Application Publication, Tokukai, No. 2012-38510 (Publication Date: Feb. 23, 2012)
[Patent Literature 4]
Japanese Registered Utility Model No. 3112435 (Publication Date: Aug. 11, 2005)
[Patent Literature 5]
Japanese Registered Utility Model No. 3174998 (Publication Date: Apr. 19, 2012)

SUMMARY OF INVENTION

Technical Problems

Note here that during manufacture of an ion generating device, members of the ion generating device are preferably partially sealed with a resin for insulation protection against a high voltage. For example, an ion generating device can be arranged such that a base end part of a mounting part for mounting a discharge electrode on a substrate is sealed with a resin.

Note, however, that as specifically described later, sealing of a base end part of a mounting part with a resin causes a resin material to adhere to a discharge electrode, so that performance of an ion generating device may be degraded.

The present invention has been made in view of the problem, and an object of the present invention is to reduce a risk of performance degradation caused to an ion generating device that is being manufactured.

Solution to Problem

In order to attain the object, an ion generating device includes: a discharge electrode for generating ions by electric discharge, the discharge electrode having (i) a mounting part for mounting the discharge electrode on the ion generating device and (ii) a brush part including a plurality of linear electrically conductive members, and the mounting part binding a base end part of the brush part so as to hold the base end part, the ion generating device further including: a first resin with which to seal the base end part of the mounting part; and a second resin with which to cover at least a base end surface of the brush part.

Advantageous Effects of Invention

An ion generating device in accordance with an aspect of the present invention makes it possible to yield an effect of reducing a risk of performance degradation caused to an ion generating device that is being manufactured.

BRIEF DESCRIPTION OF DRAWINGS

FIG. 1a is a front view illustrating an arrangement of a discharge electrode and its vicinity of an ion generating device in accordance with Embodiment 1 of the present invention.

FIG. 1b is a side view illustrating the arrangement of the discharge electrode and its vicinity of the ion generating device illustrated in FIG. 1a.

FIG. 3a is a front view schematically illustrating the arrangement of the ion generating device in accordance with Embodiment 1 of the present invention.

FIG. 3b is a plan view schematically illustrating the arrangement of the ion generating device illustrated in FIG. 3a.

FIG. 3c is a side view schematically illustrating the arrangement of the ion generating device illustrated in FIG. 3a.

FIG. 6a is a front view, a plan view, and a side view each schematically illustrating the arrangement of the ion generating device in accordance with Embodiment 2 of the present invention.

FIG. 6b is a plan view schematically illustrating the arrangement of the ion generating device illustrated in FIG. 6a.

FIG. 6c is a front view, a plan view, and a side view each schematically illustrating the arrangement of the ion generating device illustrated in FIG. 6a.

DESCRIPTION OF EMBODIMENTS

Embodiment 1

Figure 1:
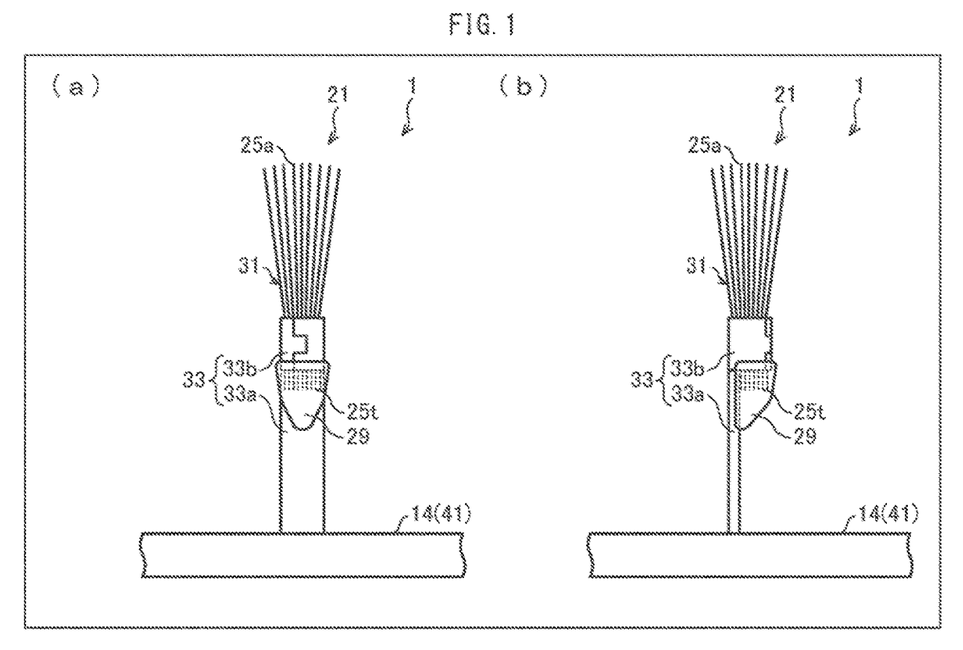
Figure 2:
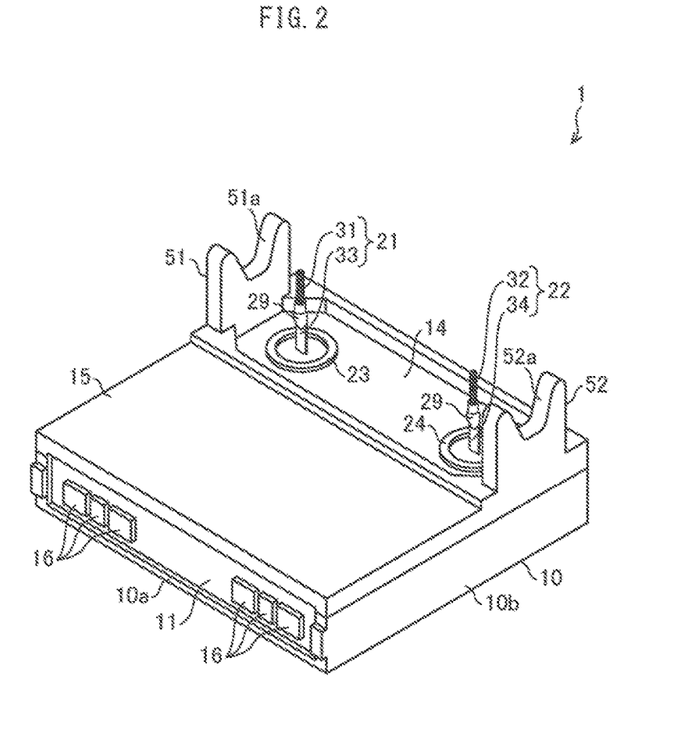
FIG. 2 is a perspective view schematically illustrating an arrangement of the ion generating device in accordance with Embodiment 1 of the present invention.
Figure 3:
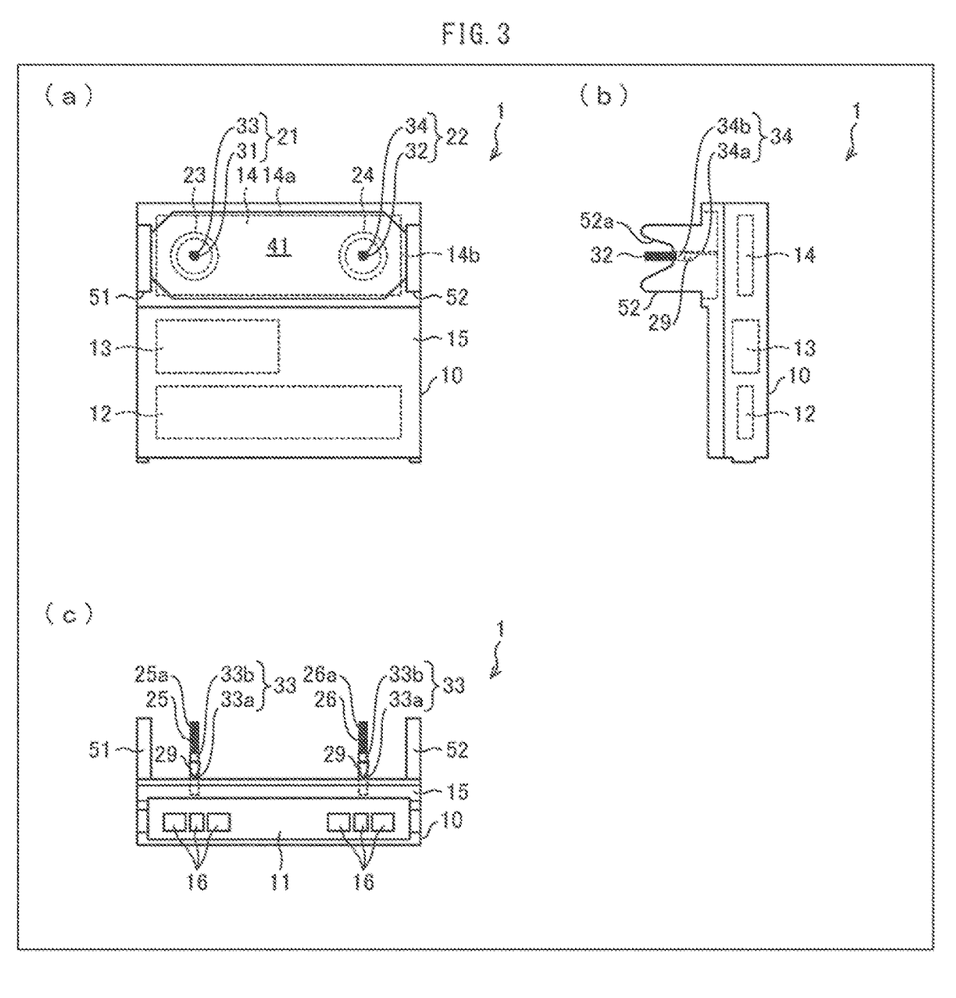

Embodiment 1 of the present invention is described below with reference to FIG. 1 through FIG. 4. First, an arrangement of an ion generating device 1 is schematically described with reference to FIG. 2 and FIG. 3. FIG. 2 is a perspective view schematically illustrating the arrangement of the ion generating device 1. FIG. 3 is a front view, a plan view, and a side view each schematically illustrating the arrangement of the ion generating device 1.

As illustrated in FIG. 2 and FIG. 3, an ion generating device 1 includes a case 10 (housing), which is quadrangular, a substrate 12 for a transformer drive circuit (hereinafter referred to as a "transformer drive circuit substrate 12"), a high voltage transformer 13 (high voltage circuit), a substrate 14 for an ion generating element (hereinafter referred to as an "ion generating element substrate 14"), a lid 15, discharge electrodes 21 and 22, and protective plates 51 and 52 (protruding members).

The case 10 is box-shaped, has a front surface and an upper surface, each of which is open, and is made of an insulating resin. The case 10 has a front part that is provided with a substrate 11 for external connection (hereinafter referred to as an "external connection substrate 11"). The case 10 contains therein the transformer drive circuit substrate 12, the high voltage transformer 13, and the ion generating element substrate 14, which are arranged in this order from the front side. The case 10 has an upper surface to which the lid 15 is provided so as to cover the external connection substrate 11, the transformer drive circuit substrate 12, and the high voltage transformer 13.

The external connection substrate 11 has a surface that is provided with a plurality of (e.g., six) connection terminals 16. Each of the plurality of connection terminals 16 is made of an electrically conductive film provided on the surface of the external connection substrate 11 and is formed by, for example, print patterning, plating, sputtering, or chemical vapor deposition (CVD). The electrically conductive film is made of a material such as copper (Cu), aluminum (Al), gold (Au), or an alloy of copper (Cu), aluminum (Al), and gold (Au), and has a thickness of an order of several ten μm (e.g., a thickness of 35 μm). The connection terminals 16 are provided so as to be exposed on an outside of the case 10 while the external connection substrate 11 is being supported by the case 10.

The transformer drive circuit substrate 12 is provided with a high voltage transformer drive circuit. The high voltage transformer drive circuit is directed to drive the high voltage transformer 13 by an externally inputted voltage.

The high voltage transformer 13 is directed to be driven by the high voltage transformer drive circuit so as to raise a voltage supplied thereto. The ion generating element substrate 14 is provided with an ion generating element. The ion generating element is directed to generate at least either of positive ions and negative ions in response to application thereto the voltage raised by the high voltage transformer 13.

The ion generating element includes discharge electrodes 21 and 22 and induction electrodes 23 and 24, which are circular. The discharge electrode 21 is provided to one side part of the ion generating element substrate 14, and the induction electrode 23 is provided around a place where the discharge electrode 21 is provided. The discharge electrode 22 is provided to the other side part of the ion generating element substrate 14, and the induction electrode 24 is provided around a place where the discharge electrode 22 is provided.

The induction electrode 23 is an electrode for forming an electric field between the induction electrode 23 and the discharge electrode 21, and the induction electrode 24 is an electrode for forming an electric field between the induction electrode 24 and the discharge electrode 22. The discharge electrode 21 is an electrode for generating negative ions between the discharge electrode 21 and the induction electrode 23, whereas the discharge electrode 22 is an electrode for generating positive ions between the discharge electrode 22 and the induction electrode 24. Note that the induction electrodes 23 and 24 each have ground electric potential.

As illustrated in FIG. 3, the ion generating element substrate 14 has a surface that is covered with an insulating sealing member 41 (first resin, mold resin). The insulating sealing member 41 can be an insulating material such as a heat-curable epoxy resin. The insulating sealing member 41 can be formed by heating a resin material and causing the resin material to cure.

With the insulating sealing member 41, base end parts of mounting parts 33a and 34a of the discharge electrodes 21 and 22 are sealed. Note that as described later, the mounting parts 33a and 34a are members for mounting the respective discharge electrodes 21 and 22 on the ion generating device 1 (more specifically, the ion generating element substrate 14). In a case where the insulating sealing member 41 is provided, the mounting parts 33a and 34a can be provided with insulation protection against a high voltage.

The ion generating element substrate 14 has a surface that is covered with an insulating sealing member 41 whose surface, for example, substantially do not differ in level from a surface of the lid 15. The discharge electrodes 21 and 22, which are provided so as to perpendicularly extend from the surface of the ion generating element substrate 14, protrude from the surface of the insulating sealing member 41.

The discharge electrode 21 is a brush-like discharge electrode including a plurality of linear electrically conductive members 25. The discharge electrode 21 has a tip part 31 formed like a brush; and a base end part 33 to which the plurality of linear electrically conductive members 25 is attached. The discharge electrode 22 is a brush-like discharge electrode including a plurality of linear electrically conductive members 26. The discharge electrode 22 has a tip part 32 formed like a brush; and a base end part 34 to which the plurality of electrically conductive members 26 is attached.

Note that the tip parts 31 and 32 refer to parts located ahead of the respective base end parts 33 and 34. Specifically, the tip part 31 refers to a part that extends from a respective plurality of tips 25a of the plurality of electrically conductive members 25, which is a brush-like bundle, to a connection end (contact end) of the plurality of electrically conductive members 25 at which connection end (contact end) the plurality of electrically conductive members 25 is in connection (in contact) with the base end part 33. The tip part 32 refers to a part that extends from a respective plurality of tips 26a of the plurality of electrically conductive members 26, which is a brush-like bundle, to a connection end (contact end) of the plurality of electrically conductive members 26 at which connection end (contact end) the plurality of electrically conductive members 26 is in connection (in contact) with the base end part 34. Examples of the term "linear" include terms such as "thready", "fibrous", and "wiry".

The tip parts 31 and 32 of the discharge electrodes 21 and 22 are made of an electrically conductive member such as metal, carbon fiber, electrically conductive fiber, or electrically conductive resin. The plurality of electrically conductive members 25 of the tip part 31 and the plurality of electrically conductive members 26 of the tip part 32 each have an outside diameter of not less than 5 μm and not more than 30 μm. In a case where the plurality of electrically conductive members 25 and the plurality of electrically conductive members 26 each have an outside diameter of not less than 5 μm, the plurality of electrically conductive members 25 and the plurality of electrically conductive members 26 can be mechanically strong and also can be prevented from being electrically worn. Meanwhile, in a case where the plurality of electrically conductive members 25 and the plurality of electrically conductive members 26 each have an outside diameter of not more than 30 μm the plurality of electrically conductive members 25 and the plurality of electrically conductive members 26 are bent like hair, so that the plurality of electrically conductive members 25 and the plurality of electrically conductive members 26 easily spread and easily sway.

The plurality of electrically conductive members 25 and the plurality of electrically conductive members 26 each can be a carbon fiber having an outside diameter of 7 μm, or an electrically conductive fiber made of stainless steel (SUS) and having an outside diameter of 12 μm or 25 μm.

The base end part 33 of the discharge electrode 21 has (i) the mounting part 33a, which is sheet metal, for mounting the discharge electrode 21 on the ion generating element substrate 14 and (ii) a binding part 33b for binding the plurality of electrically conductive members 25 of the tip part 31 at the connection end. As in the case of base end part 33 of the discharge electrode 21, the base end part 34 of the discharge electrode 22 has (i) the mounting part 34a, which is sheet metal, for mounting the discharge electrode 22 on the ion generating element substrate 14 and (ii) a binding part 34b for binding the plurality of electrically conductive members 26 of the tip part 32 at the connection end.

Figure 4:
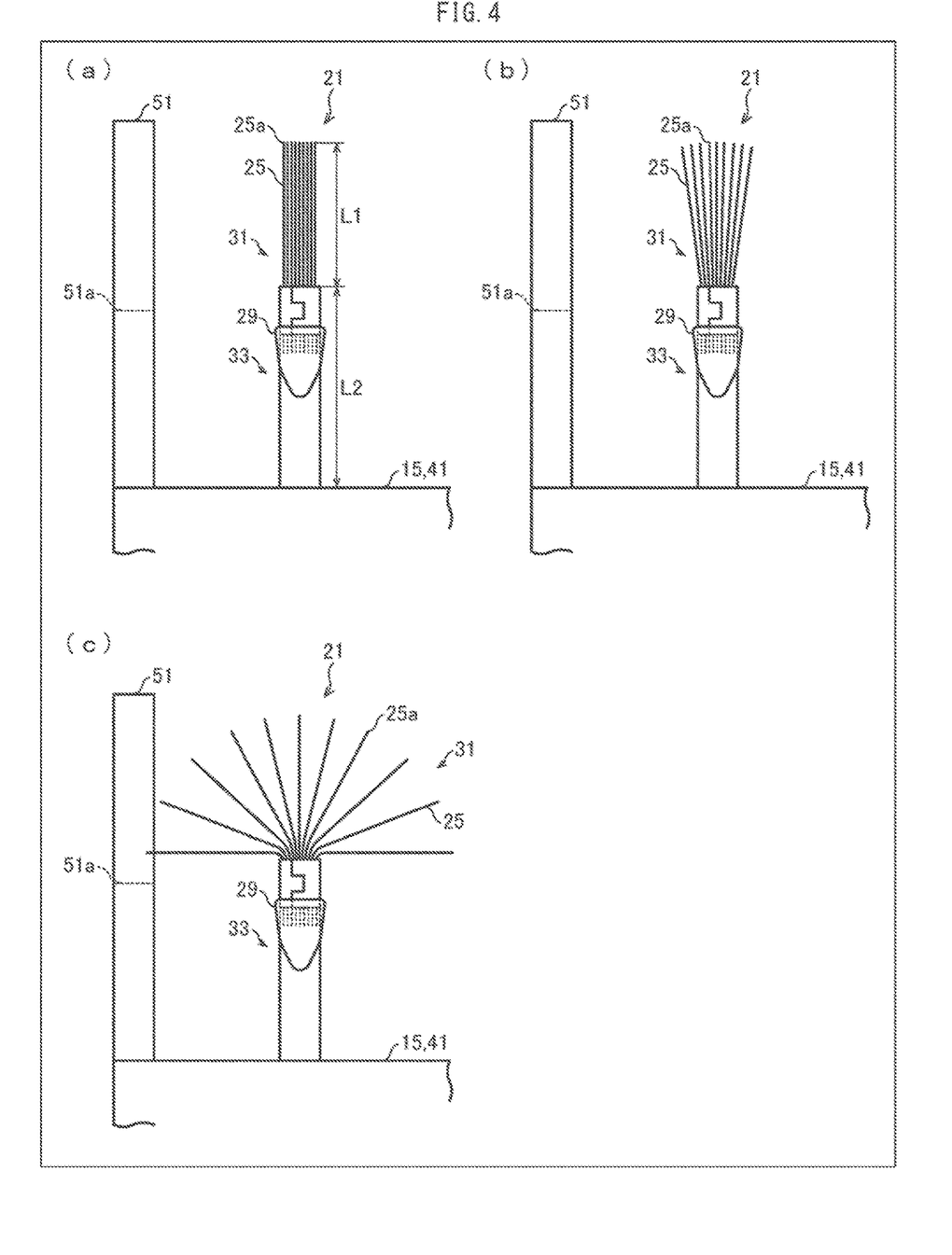
FIG. 4a is a front view schematically illustrating an arrangement of a discharge electrode and a protective plate which are illustrated in each of FIG. 2 and FIG. 4a, showing a state in which no voltage is applied to the discharge electrode.
FIG. 4b is a front view schematically illustrating an arrangement of a discharge electrode and a protective plate which are illustrated in each of FIG. 2 and FIG. 4b, showing a state in which a pulse having a high voltage is being applied to the discharge electrode.
FIG. 4c is a front view schematically illustrating an arrangement of a discharge electrode and a protective plate which are illustrated in each of FIG. 2 and FIG. 4c, showing a state in which a pulse having a higher voltage is being applied to the discharge electrode.

Next, a length of the tip part 31 of the discharge electrode 21 is described with reference to FIG. 4. FIG. 4 is front views each schematically illustrating an arrangement of the discharge electrode 21 and a protective plate 51 which are illustrated in each of FIG. 2 and FIG. 3. FIG. 4 illustrates how the tip part 31 of the discharge electrode 21 changes in shape in accordance with a voltage applied to the discharge electrode 21 (and between the discharge electrode 21 and the induction electrode 23). Note that same applies to the discharge electrode 22 (not illustrated in FIG. 4).

L1 shown in FIG. 4 refers to a length of the tip part 31 of the discharge electrode 21, i.e., a length (protrusion length) for which the plurality of linear electrically conductive members 25 protrudes from the base end part 33. L2 shown in FIG. 4 refers to a length (protrusion length) for which the base end part 33 of the discharge electrode 21 protrudes (is exposed) from the lid 15, i.e., the insulating sealing member 41.

(a) of FIG. 4 illustrates a state in which no voltage is applied to the discharge electrode 21. In this case, the tips of the plurality of linear electrically conductive members 25 are closed in the tip part 31 of the discharge electrode 21.

(b) of FIG. 4 illustrates a state in which a pulse having a high voltage is being applied to the discharge electrode 21. In this case, in the tip part 31 of the discharge electrode 21, the plurality of electrically conductive members 25 electrically repel each other because the electrically conductive members 25 are homopolar. This causes the electrically conductive members 25 to be bent and consequently be shaped as if a tip of a brush was opened.

Meanwhile, at the tips of the electrically conductive members 25, positive ions are generated. As described above, the electrically conductive members 25 are shaped as if the tip of the brush was opened. This results in an increase in area of a region in which positive ions are generated. Thus, the discharge electrode 21 of Embodiment 1 causes a further increase in amount of generation of ions than a needle-like discharge electrode in a case where an identical voltage is applied to each of the discharge electrode 21 and the needle-like discharge electrode.

(c) of FIG. 4 illustrates a state in which a pulse having a higher voltage is being applied to the discharge electrode 21. In this case, in the tip part 31 of the discharge electrode 21, the plurality of electrically conductive members 25 electrically further repel each other. This causes the electrically conductive members 25 to be shaped as if the tip of the brush was further opened. Thus, ions are generated in a larger amount.

The plurality of electrically conductive members 25 of the discharge electrode 21 is electrically attracted to the induction electrode 23 whose polarity is opposite from that of the plurality of electrically conductive members 25. This may cause one or more of the plurality of electrically conductive members 25 to be greatly bent toward the induction electrode 23.

In order to overcome the above problem, Embodiment 1 causes the protrusion length L1 of the electrically conductive members 25 to be shorter than the protrusion length L2 of the base end part 33. Thus, even in a case where the electrically conductive members 25 are bent by being electrically attracted to the induction electrode 23, or in a case where the electrically conductive members 25 are bent by a dynamic force (e.g., a touch by a person) exerted thereon, the electrically conductive members 25 do not contact the insulating sealing member 41. This makes it possible to prevent, without fail, (i) a trouble such that abnormal electric discharge, an electric current leakage, or the like occurs in a part of the electrically conductive members 25 in which part the electrically conductive members 25 contact the insulating sealing member 41, so that an amount of generation of ions is reduced or becomes zero, (ii) a trouble such that the transformer drive circuit substrate 12, the high voltage transformer 13, and the ion generating element substrate 14, which are contained in the case 10, are broken by occurrence therein abnormal electric discharge, an electric current leakage, or the like, and (iii) a trouble of an increase in noise figure of the ion generating device 1.

There is a case where the case 10 is made electrostatic by the high voltage transformer 13, so that a dust or the like adheres to the surface of the lid 15 or the insulating sealing member 41. In particular, in a case where the insulating sealing member 41 is a heat-curable epoxy resin or the like, a dust or the like easily adheres thereto because such an insulating sealing member 41 has a high frictional resistance. In view of this, abnormal electric discharge, an electric current leakage, or the like (described earlier) may occur. In order to overcome the above problem, Embodiment 1 makes it possible to prevent abnormal electric discharge, an electric current leakage, or the like from occurring in the part of the electrically conductive members 25 in which part the electrically conductive members 25 contact the insulating sealing member 41.

Note that the length of the tip parts 31 and 32 of the discharge electrodes 21 (the protrusion length L1 of the electrically conductive members 25 and the electrically conductive members 26) is not particularly limited provided that the length is set to be shorter than the protrusion length L2 of the base end parts 33 and 34 as described earlier. Note, however, that the tip parts 31 and 32 whose length is too short make it difficult for the electrically conductive members 25 and the electrically conductive members 26 to be bent. This causes the electrically conductive members 25 and the electrically conductive members 26 to less spread and less sway, so that an effect of the brush-like discharge electrode cannot be sufficiently obtained. The tip parts 31 and 32 which have a longer length make the ion generating device 1 larger in size.

Thus, the tip parts 31 and 32 desirably have a length of not less than 3 mm. Note that the tip parts 31 and 32 can also have a length of not less than 5 mm. The protrusion length L2 of the base end parts 33 and 34 is desirably not more than 5 times longer than the length of the tip parts 31 and 32 (the protrusion length L1 of the electrically conductive members 25 and the electrically conductive members 26).

Next, the protective plates 51 and 52 are described with reference to FIG. 2 through FIG. 4. The ion generating device 1 is not necessarily placed, during a period in which the ion generating device 1 has been produced and then is mounted in various electrical apparatuses, on a base on which to place the ion generating device 1 (hereinafter, the "base" is referred to as a "placing base", not illustrated) in such a state as illustrated in each of FIG. 2 and FIG. 3. For example, the ion generating device 1 which is placed on the placing base in such a state as illustrated in each of FIG. 2 and FIG. 3 may be turned upside down so as to be placed on the placing base.

As described above, overturning of the ion generating device 1 during, for example, a production process may cause breakage (deformation) such as a break in a brush part which break is caused by a contact between (a) the discharge electrodes 21 and 22 and (b) a floor such as the placing base.

In order to overcome the above problem, Embodiment 1 is arranged such that the protective plates 51 and 52 for protecting the respective discharge electrodes 21 and 22 protrude so as to be adjacent to the respective discharge electrodes 21 and 22. Note that according to Embodiment 1, the ion generating element substrate 14 in which the discharge electrodes 21 and 22 protrude is provided in an end of a rear part of the upper surface of the case 10, which is quadrangular.

The ion generating element substrate 14 is rectangular, and the discharge electrodes 21 and 22 are arranged in a longer side direction of the ion generating element substrate 14. The ion generating element substrate 14 has a long side 14a that (i) is a side parallel to the direction in which the discharge electrodes 21 and 22 are arranged and (ii) faces a side 10a of the rear part of the case 10 so as to be parallel to the side 10a.

In view of the above, according to Embodiment 1, on both ends of the rear part of the upper surface of the case 10, the protective plates 51 and 52 protrude so as to be adjacent to the respective discharge electrodes 21 and 22.

The protective plates 51 and 52 are juxtaposed to each other while the discharge electrodes 21 and 22 are sandwiched therebetween in the longer side direction of the ion generating element substrate 14 (i.e., a direction parallel to the long side 14a of the ion generating element substrate 14), which longer side direction is the direction in which the discharge electrodes 21 and 22 are arranged.

The protective plates 51 and 52 have a height whose maximum value is greater than a height of the discharge electrodes 21 and 22. The protective plates 51 and 52 vertically protrude, on the insulating sealing member 41 or in an upper part of the lid 15, or by being integrally molded with the lid 15, so as to further protrude from the surface of the ion generating element substrate 14 than the tip parts 31 and 32 of the discharge electrodes 21 and 22.

With the arrangement, even in a case where the ion generating device 1 is, for example, overturned, the discharge electrodes 21 and 22 can be prevented from directly contacting an object, provided on an outside of the ion generating device 1, such as the placing base, so that the discharge electrodes 21 and 22 can be prevented from, for example, being broken by the contact.

Note here that the height of the protective plates 51 and 52 refers to a vertical length, i.e., a height from the surface of the insulating sealing member 41 to an upper surface of the protective plate 51 as well as a height from the surface of the insulating sealing member 41 to an upper surface of the protective plate 52.

The height of the protective plates 51 and 52 is not particularly limited provided that the protective plates 51 and 52 further protrude from the surface of the ion generating element substrate 14 than the tip parts 31 and 32 of the discharge electrodes 21 and 22.

Note, however, that the protective plates 51 and 52 which have a greater height make the ion generating device 1 larger in size accordingly. Thus, the protective plates 51 and 52 desirably have a height that is great enough for the discharge electrodes 21 and 22 to be prevented from directly contacting the object, provided on the outside of the ion generating device 1, such as the placing base in a case where the ion generating device 1 is, for example, overturned.

For example, the height from the surface of the insulating sealing member 41 to the upper surfaces of the protective plates 51 and 52 is desirably slightly greater than a height from the surface of the insulating sealing member 41 to tips of the tip parts 31 and 32 (i.e., a maximum value of a height from the surface of the insulating sealing member 41 to the tips 25a and 26a of the electrically conductive members 25 and the electrically conductive members 26) in the discharge electrodes 21 and 22.

The protective plates 51 and 52 are spaced from the respective discharge electrodes 21 and 22 so that a distance between the discharge electrode 21 and the protective plate 51 and a distance between the discharge electrode 22 and the protective plate 52 are each longer than the length of the tip parts 31 and 32 of the discharge electrodes 21 and 22.

Thus, as illustrated in (b) and (c) of FIG. 4, even in a case where the electrically conductive members 25 or the electrically conductive members 26 repel each other and the tip part 31 or 32 spreads, so that the electrically conductive members 25 or the electrically conductive members 26 lean at any angle, the electrically conductive members 25 and the electrically conductive members 26 do not directly contact the respective protective plates 51 and 52. This makes it possible to prevent occurrence of a leakage.

When the discharge electrodes 21 and 22 are seen through the respective protective plates 51 and 52 (i.e., when the ion generating device 1 is seen from a direction parallel to the side 10a of the case 10), respective parts of the protective plates 51 and 52 which parts face the respective tip parts 31 and 32 of the discharge electrodes 21 and 22 are each formed in a shape of a notched plate. Thus, the protective plate 51 is provided with an opening 51a, facing the discharge electrode 21, for exposing the tip part 31. Meanwhile, the protective plate 52 is provided with an opening 52a, facing the discharge electrode 22, for exposing the tip part 32.

The protective plates 51 and 52, which are thus provided with the respective openings 51a and 52a, do not inhibit the discharge electrodes 21 and 22 from releasing ions, so that the ions can be satisfactorily released.

According to Embodiment 1, the mounting parts 33a and 34a, which are plate-like, are mounted on the ion generating element substrate 14 so that a direction normal to plate surfaces of the mounting parts 33a and 34a is a front and rear direction. It is easy for the electrically conductive members 25 and the electrically conductive members 26 to lean in a direction in which the sheet metal mounting parts 33a and 34a have a small thickness, whereas it is difficult for the electrically conductive members 25 and the electrically conductive members 26 to lean in a direction in which the sheet metal mounting parts 33a and 34a have a great thickness. Thus, it is easy for the discharge electrodes 21 and 22 to lean in the front and rear direction, whereas it is difficult for the discharge electrodes 21 and 22 to lean in a right and left direction. This prevents the protective plates 51 and 52, which are provided in the right and left direction of the discharge electrodes 21 and 22, from being in proximity to the electrically conductive members 25 and the electrically conductive members 26 of the discharge electrodes 21 and 22, so that a leakage can be effectively prevented.

In other words, the plate-like mounting parts 33a, and 34a of the discharge electrodes 21 and 22 are desirably mounted on the ion generating element substrate 14 so that the protective plates 51 and 52 are absent in the direction normal to the plate surfaces of the mounting parts 33a and 34a.

Next, an arrangement of a vicinity of a discharge electrode of Embodiment 1 is more specifically described with reference to FIG. 1. FIG. 1 is illustrates an arrangement of the discharge electrode and its vicinity, (a) of FIG. 1 is a front view illustrating the arrangement of the discharge electrode and its vicinity, and (b) of FIG. 1 is a side view illustrating the arrangement of the discharge electrode and its vicinity. In FIG. 1, the discharge electrode 21 is taken as an example of the discharge electrode. Note, however, that the following description also applies to the discharge electrode 22.

As described earlier, the binding part 33b holds a base end part of a brush (may also be referred to as a "brush part") so as to bind (caulk) the base end part, the brush including the plurality of linear electrically conductive members 25. The mounting part 33a has a base end part that is sealed with the insulating sealing member 41.

As illustrated in FIG. 1, the base end part of the brush, which base end part is bound by the binding part 33b, is covered with a protective resin 29 (second resin). The protective resin 29 is a member with which to cover at least a base end surface of the brush.

In FIG. 1, assume that the base end surface of the brush is referred to as a brush base end surface 25t. The protective resin 29 can be, for example, a resin material such as an ultraviolet (UV) curable resin. The protective resin 29 can be formed by irradiating the resin material with ultraviolet rays and causing the resin material to cure.

The following description discusses an advantage of provision of the protective resin 29. As described earlier, the linear electrically conductive members 25 each have an extremely small outside diameter (e.g., 7 μm). In other words, the electrically conductive members are each shaped to be extremely long and narrow.

Thus, in a case where a liquid adheres to the base end part (e.g., the brush base end surface 25t) of the brush, in which base end part the plurality of linear electrically conductive members 25 are bound together, a considerable capillary force is generated between the respective electrically conductive members 25, so that the liquid permeates into an upper part of the brush by the capillary force.

In order to enhance insulation performance of the insulating sealing member 41, it is preferable to provide, during manufacture of the insulating sealing member 41, a step for allowing the insulating sealing member 41 to have a better quality. For example, the step can be a process (a second step (described later)) of vacuum defoaming a resin material (a material of the insulating sealing member 41) with which to seal the base end part of the mounting part 33a.

In a case where the resin material is vacuum defoamed in the above process, it is possible to prevent a void from being created inside the insulating sealing member 41. This makes it possible to enhance insulation performance of the insulating sealing member 41.

Note, however, that the resin material which is vacuum defoamed may (i) cause air bubbles in the resin material to be discharged and (ii) cause the resin material to be scattered. Thus, in a case where the resin material which has been scattered adheres to the base end part of the brush, the resin material permeates into the upper part of the brush by a capillary force.

Then, in a case where the resin material which has permeated into the upper part of the brush cures, the linear electrically conductive members 25 are prevented from spreading. This reduces ion generating capability of the discharge electrode 21. That is, a trouble of a decrease in performance of the ion generating device 1 occurs.

In view of the above, the protective resin 29 is provided in Embodiment 1 so that the above trouble is prevented. Note that the protective resin 29 is provided as a member of the ion generating device 1 in advance before the vacuum defoaming process (described earlier) is carried out. As described earlier, since the brush base end surface 25t is covered with the protective resin 29, a foreign matter (liquid) can be prevented from adhering to the brush base end surface 25t.

As described earlier, according to the ion generating device 1 of Embodiment 1, which ion generating device 1 is provided with the protective resin 29, even the resin material which is scattered can be prevented from adhering to the brush base end surface 25t. This makes it possible to reduce a risk of performance degradation caused to the ion generating device which is being manufactured.

Note that the protective resin 29, which also functions as an adhesive, brings about an advantage of allowing the base end part of the brush to be more firmly bound. Note here that in order to explain the above advantage, the following description discusses a case where no protective resin 29 is provided.

In this case, the base end part of the brush is bound only by the binding part 33*b*. Thus, in a case where one electrically conductive member 25 falls out of the binding part 33*b*, the binding part 33*b* has a lower binding force (force with which to bind the base end part of the brush).

Such a decrease in binding force causes the electrically conductive members 25 to more easily fall out of the binding part 33*b*. Thus, in a case where even one electrically conductive member 25 falls out, more electrically conductive members 25 easily fall out due to the decrease in binding force, so that all the electrically conductive members 25 may fall out of the binding part 33*b*.

Note, however, that the ion generating device 1 of Embodiment 1 is arranged such that the protective resin 29 is provided so that at least the brush base end surface 25*t* is covered therewith. This allows not only the binding part 33*b* but also the protective resin 29 to hold the base end part of the brush. Thus, the advantage of allowing the base end part of the brush to be more firmly bound can be brought about as described earlier.

The protective resin 29 which has not cured preferably has a viscosity that is higher than a viscosity of the insulating sealing member 41 which has not cured. For example, the insulating sealing member 41 which has not cured has a viscosity of 1.6 Pa·s, and the protective resin 29 which has not cured has a viscosity of 30 Pa·s. The protective resin 29 which has not cured is thus understood to have a much higher (approximately 18 times higher) viscosity than the insulating sealing member 41 which has not cured.

With the arrangement, the viscosity of the protective resin 29 which has not cured is higher than the viscosity of the insulating sealing member 41 which has not cured. This makes it possible to prevent even the protective resin 29 which has not cured from rapidly permeating into the upper part of the brush by a capillary force.

Specifically, the protective resin 29 can be prevented from permeating into the upper part of the brush by a capillary force during a step of forming the protective resin 29 (a third step (described later), e.g., a step of causing curing of the protective resin 29 by irradiating a resin material of the protective resin 29 with ultraviolet rays). This makes it possible to more reliably prevent a decrease in ion generating capability of the discharge electrode 21.

Since the viscosity of the protective resin 29 which has not cured is higher than the viscosity of the insulating sealing member 41 which has not cured, even in a case where the protective resin 29 which has not cured permeates from the brush base end surface 25*t*, permeation of the protective resin 29 from the brush base end surface 25*t* is slow. This makes it easy for the protective resin 29 to cure in the base end part of the brush and stop permeating. Thus, since the protective resin 29 does not permeate into the upper part of the brush, it is possible to prevent a decrease in ion generating capability of the discharge electrode.

Note that a method for manufacturing the ion generating device 1 of Embodiment 1 can be expressed as below. Specifically, the method includes the steps of: a) providing the discharge electrode 21 with the protective resin 29 (a first step); b) after the step a), vacuum defoaming a resin material with which to seal the base end part of the mounting part 33*a* (the second step); and c) forming the insulating sealing member 41 by causing the resin material which has been vacuum defoamed to cure (the third step).

As described earlier, in a case where the protective resin 29 is formed in advance in the first step (e.g., the step of irradiating the protective resin 29 which has not cured with ultraviolet rays), even the resin material which is scattered during the second step can be prevented from adhering to the brush base end surface 25*t*.

Thus, the insulating sealing member 41 which has a high quality (is excellent in insulation performance) can be formed in the third step without performance degradation of the ion generating device. The method described earlier thus makes it possible to manufacture the ion generating device 1 without performance degradation of the ion generating device 1.

[Variation]

The description of Embodiment 1 takes, as an example, a case where the protective plates 51 and 52 are juxtaposed to each other while the discharge electrodes 21 and 22 are sandwiched therebetween in the longer side direction of the ion generating element substrate 14. Note, however, that Embodiment 1 is not limited to this.

It is possible to provide only one protective plate provided that the protective plate is provided at a location and a height that allow the electrically conductive members 25 and the electrically conductive members 26 to be prevented from directly contacting the object, provided on the outside of the ion generating device 1, even in a case where the ion generating device 1 is, for example, overturned.

The description of Embodiment 1 also takes, as an example, a case where the ion generating element substrate 14 is provided in the rear part of the case 10. Note, however, that the ion generating element substrate 14 can also be provided in the front part or a central part of the case 10.

Note that positive ions and negative ions can be generated by the discharge electrodes 21 and 22 even in a case where the induction electrodes 23 and 24, which are used in Embodiment 1, are not used. Note, however, that use of the induction electrodes 23 and 24 is desirable. This is because use of the induction electrodes 23 and 24 causes a further increase in (i) electric field intensity of the discharge electrodes 21 and 22 and (ii) amount of generation of ions than non-use of the induction electrodes 23 and 24.

Embodiment 2

Embodiment 2 of the present invention is described below with reference to FIG. 5 and FIG. 6. Embodiment 2 describes points of difference from Embodiment 1. Note that for convenience, members having functions identical to those of the respective members described in Embodiment 1 are given respective identical reference numerals, and a description of those members is omitted.

Figure 5:
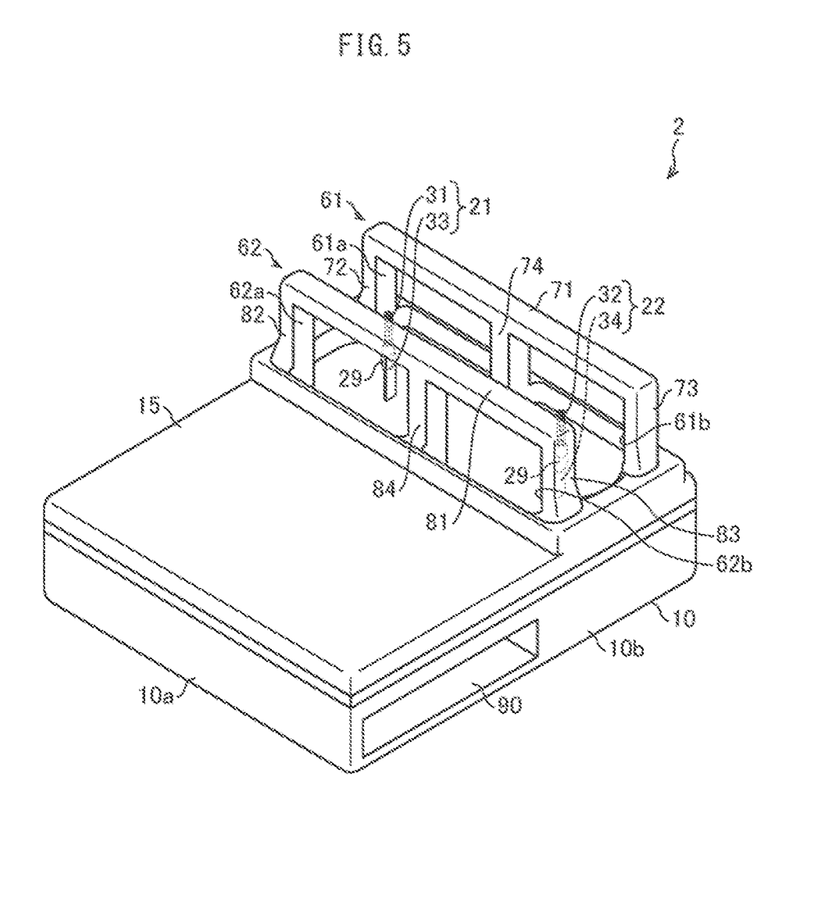
FIG. 5 is a perspective view schematically illustrating an arrangement of an ion generating device in accordance with Embodiment 2 of the present invention.

FIG. 5 is a perspective view schematically illustrating an arrangement of an ion generating device 2 of Embodiment 2. FIG. 6 is a front view, a plan view, and a side view each schematically illustrating the arrangement of the ion generating device 2.

The ion generating device 2 is arranged as in the case of the ion generating device 1 in accordance with Embodiment 1 except (i) that in Embodiment 2, protective plates 61 and 62 (protruding members) for protecting discharge electrodes 21 and 22, instead of the protective plates 51 and 52, are juxtaposed to each other while the discharge electrodes 21 and 22 are sandwiched therebetween in a shorter side direction of an ion generating element substrate 14 (i.e., a direction parallel to a short side 14*b* of the ion generating element substrate 14), which shorter side direction is perpendicular to a direction in which the discharge electrodes 21 and 22 are arranged, and mounting parts 33a and 34a of the discharge electrodes 21 and 22 tend to lean in a direction different from a direction in which the mounting parts 33a and 34a of Embodiment 1 tend to lean and (ii) that in Embodiment 2, a case 10 has a side surface provided with a recess 90 instead of the external connection substrate 11, and the recess 90 is provided with a plurality of connection terminals 91.

The protective plates 61 and 62 have a height whose maximum value is greater than a height of the discharge electrodes 21 and 22. The protective plates 61 and 62 vertically protrude, on an insulating sealing member 41 or in an upper part of a lid 15, or by being integrally molded with the lid 15, so as to further protrude from a surface of the ion generating element substrate 14 than tip parts 31 and 32 of the discharge electrodes 21 and 22.

With the arrangement, also according to Embodiment 2, even in a case where the ion generating device 2 is, for example, overturned, the discharge electrodes 21 and 22 can be prevented from directly contacting an object, provided on an outside of the ion generating device 2, such as a placing base, so that the discharge electrodes 21 and 22 can be prevented from, for example, being broken by the contact.

Note here that the height of the protective plates 61 and 62 refers to a vertical length, i.e., a height from a surface of the insulating sealing member 41 to an upper surface of the protective plate 61 as well as a height from the surface of the insulating sealing member 41 to an upper surface of the protective plate 62. Note also that the upper surfaces of the protective plates 61 and 62 specifically refer to upper surfaces of beam parts 71 and 81 (described later).

Also according to Embodiment 2, the height of the protective plates 61 and 62 is not particularly limited as in the case of the protective plates 51 and 52 provided that the protective plates 61 and 62 further protrude from the surface of the ion generating element substrate 14 than the tip parts 31 and 32 of the discharge electrodes 21 and 22.

Note, however, that the protective plates 61 and 62 which have a greater height make the ion generating device 2 larger in size accordingly. Thus, the protective plates 61 and 62 desirably have a height that is great enough for the discharge electrodes 21 and 22 to be prevented from directly contacting the object, provided on the outside of the ion generating device 2, such as the placing base in a case where the ion generating device 2 is, for example, overturned.

For example, the height from the surface of the insulating sealing member 41 to the upper surfaces of the protective plates 61 and 62 is desirably slightly greater than a height from the surface of the insulating sealing member 41 to tips of the tip parts 31 and 32 (i.e., a maximum value of a height from the surface of the insulating sealing member 41 to tips 25a and 26a of electrically conductive members 25 and electrically conductive members 26) in the discharge electrodes 21 and 22.

In order that a distance between (a) the discharge electrode 21 or the discharge electrode 22 and (b) the protective plate 61 or the protective plate 62 is longer than a length of the tip parts 31 and 32 of the discharge electrodes 21 and 22, the protective plates 61 and 62 are provided so as to face each other while being spaced from each other.

Specifically, the protective plates 61 and 62 are adjacent to each other so that a distance therebetween is not less than two times longer than the length of the tip parts 31 and 32 of the discharge electrodes 21 and 22. Thus, according to Embodiment 2, even in a case where the electrically conductive members 25 or the electrically conductive members 26 repel each other and the tip part 31 or 32 spreads, so that the electrically conductive members 25 or the electrically conductive members 26 lean at any angle, the electrically conductive members 25 and the electrically conductive members 26 do not directly contact the protective plates 61 and 62. This makes it possible to prevent occurrence of a leakage.

Figure 6:
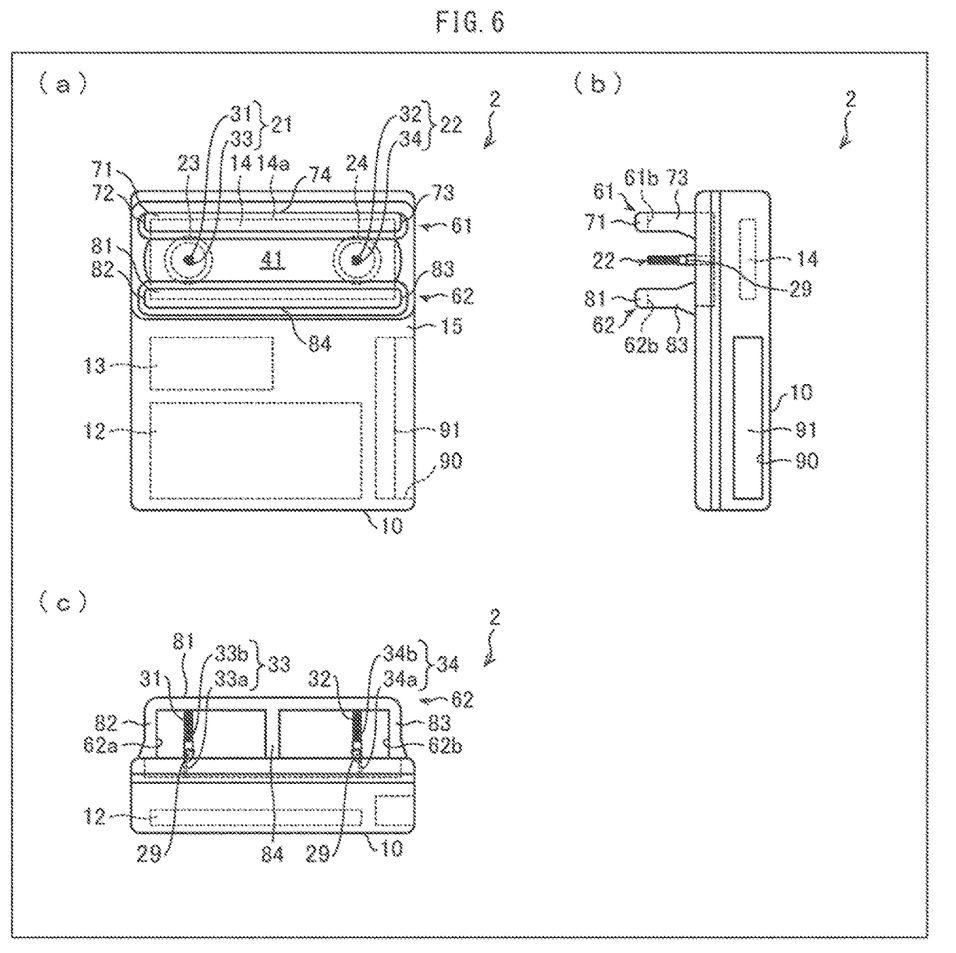

For example, the tip parts 31 and 32 illustrated in each of FIG. 5 and FIG. 6 may decrease in amount of electric discharge due to adhesion of, for example, a dust to the electrically conductive members 25 and the electrically conductive members 26 which adhesion is caused by static electricity generated by electric discharge. Thus, there is a case where the ion generating device 2 which is provided in an electrical apparatus is removed by a user so that cleaning is carried out for removing, for example, a dust from the electrically conductive members 25 and the electrically conductive members 26 of the tip parts 31 and 32.

Note here that an upper limit of the distance between the protective plates 61 and 62 is not particularly limited provided that the distance is not less than two times longer than the length of the tip parts 31 and 32 of the discharge electrodes 21 and 22. Note, however, that the distance between the protective plates 61 and 62 is desirably set at a distance that prevents a finger of the user from touching the electrically conductive members 25 and the electrically conductive members 26 of the tip parts 31 and 32. This makes it possible to prevent a finger of the user from touching the electrically conductive members 25 and the electrically conductive members 26 of the tip parts 31 and 32.

The protective plates 61 and 62 are each formed like glasses. Specifically, the protective plate 61 has a beam part 71 that is made of a horizontally long plate parallel to the surface of the ion generating element substrate 14, support parts 72 and 73 that are supports for supporting both ends of the beam part 71, and a support part 74 that is a support for supporting a central part of the beam part 71.

A space between the support parts 72 and 74, which are adjacent to each other, and a space between the support parts 74 and 73, which are adjacent to each other, are opened. Thus, the protective plate 61 is provided with two openings 61a and 61b.

As In the case of the protective plate 61, the protective plate 62 has a beam part 81 that is made of a horizontally long plate parallel to the surface of the ion generating element substrate 14, support parts 82 and 83 that are supports for supporting both ends of the beam part 81, and a support part 84 that is a support for supporting a central part of the beam part 81.

A space between the support parts 82 and 84, which are adjacent to each other, and a space between the support parts 84 and 83, which are adjacent to each other, are opened. Thus, the protective plate 62 is provided with two openings 62a and 62b.

The support parts 72 and 73 protrude at both ends of the ion generating element substrate 14 in a longer side direction of the ion generating element substrate 14 so as to face each other. The support part 74 protrudes in a central part of the ion generating element substrate 14 in the longer side direction of the ion generating element substrate 14 so as to face each of the support parts 72 and 73.

As in the case of the support parts 72 and 73, the support parts 82 and 83 protrude at both ends of the ion generating element substrate 14 in a longer side direction of the ion generating element substrate 14 so as to face each other. The support part 84 protrudes in a central part of the ion generating element substrate 14 in the longer side direction of the ion generating element substrate 14 so as to face each of the support parts 82 and 83.

With the arrangement, the beam parts 71 and 81 are each provided so as to be parallel to a long side 14a of the ion generating element substrate 14 and serve as a bridge to connect one end to the other end of the ion generating element substrate 14 in the longer side direction of the ion generating element substrate 14.

When the discharge electrodes 21 and 22 are seen through protective plates 61 and 62 (i.e., when the ion generating device 2 is seen from a direction parallel to a side 10a of the case 10), the discharge electrode 21 is seen through the openings 62a and 61b, and the discharge electrode 22 is seen through the openings 62b and 61a.

These openings 61a, 61b, 62a, and 62b each function as a ventilation hole through which to cause gas, by which ions generated by the discharge electrodes 21 and 22 of the ion generating device 2 are carried, to pass.

According to the examples shown in FIG. 5 and FIG. 6, the protective plates 61 and 62 are provided at a height that causes the tips of the tip parts 31 and 32 of the discharge electrodes 21 and 22 (i.e., the tips of the electrically conductive members 25 and the electrically conductive members 26) to be hidden by the beam parts 71 and 81.

Note, however, that the height of the protective plates 61 and 62 (i.e., a height from the surface of the insulating sealing member 41 to upper surfaces of the beam parts 71 and 81) only needs to be set at a height greater than the height from the surface of the insulating sealing member 41 to the tips 25a and 26a of the electrically conductive members 25 and the electrically conductive members 26. The protective plates 61 and 62 can also be provided at a height that allows an entirety of the discharge electrode 21 to be seen through the openings 62a and 61b and allows an entirety of the discharge electrode 22 to be seen through the openings 62b and 61a.

According to Embodiment 2, as described earlier, since at least a part of the discharge electrode 21 is seen through the openings 62a and 61b and at least a part of the discharge electrode 22 is seen through the openings 62b and 61a, the protective plates 61 and 62 do not inhibit the discharge electrodes 21 and 22 from releasing ions, so that the ions can be satisfactorily released.

According to Embodiment 2, the mounting parts 33a and 34a, which are plate-like, are mounted on the ion generating element substrate 14 so that a direction normal to plate surfaces of the mounting parts 33a and 34a is a right and left direction. As described earlier, it is easy for the electrically conductive members 25 and the electrically conductive members 26 to lean in a direction in which the mounting parts 33a and 34a, which are sheet metal, have a small thickness, whereas it is difficult for the electrically conductive members 25 and the electrically conductive members 26 to lean in a direction in which the mounting parts 33a and 34a, which are sheet metal, have a great thickness.

Thus, it is easy for the discharge electrodes 21 and 22 to lean in the right and left direction, whereas it is difficult for the discharge electrodes 21 and 22 to lean in a front and rear direction. This prevents the protective plates 61 and 62, which are provided in the front and rear direction of the discharge electrodes 21 and 22, from being in proximity to the electrically conductive members 25 and the electrically conductive members 26 of the discharge electrodes 21 and 22, so that a leakage can be effectively prevented.

In other words, the plate-like mounting parts 33a and 34a of the discharge electrodes 21 and 22 are desirably mounted on the ion generating element substrate 14 so that the protective plates 61 and 62 are absent in the direction normal to the plate surfaces of the mounting parts 33a and 34a.

Thus, in a case where the protective plates 61 and 62 are provided so as to be adjacent to the discharge electrodes 21 and 22 in the direction parallel to the short side 14b of the ion generating element substrate 14 as illustrated in FIG. 5 and FIG. 6, the protective plates 61 and 62 are not in proximity to the electrically conductive members 25 and the electrically conductive members 26, so that a leakage can be effectively prevented.

It is a matter of course that Embodiment 2 can also be varied as in the case of Embodiment 1, though a description of a variation of Embodiment 2 is omitted.

Embodiment 3

Figure 7:
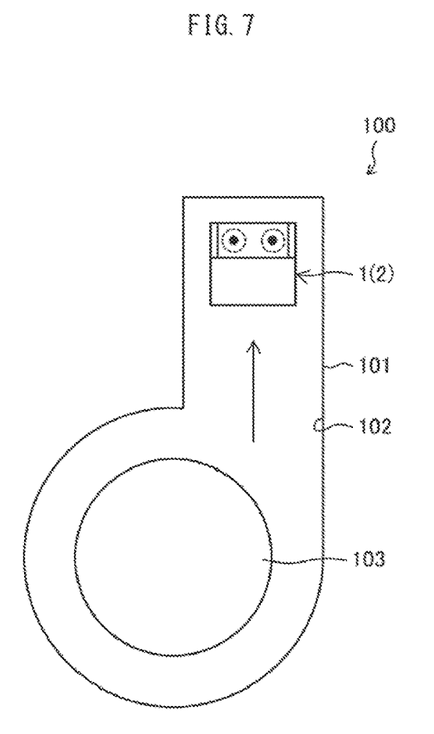
FIG. 7 is a plan view showing an example of an arrangement of an inside of an electrical apparatus in accordance with Embodiment 3 of the present invention.

Embodiment 3 of the present invention is described with reference to FIG. 7 and FIG. 8. Embodiment 3 describes an electrical apparatus including an ion generating device. FIG. 7 is a plan view showing an example of an arrangement of an inside of an electrical apparatus 100 of Embodiment 3. First, an arrangement of the electrical apparatus 100 is described with reference to FIG. 7.

Note that the following description takes, as an example, a case where an ion generating device 1 of Embodiment 1 is used as the ion generating device. Note, however, that instead of the case where the ion generating device 1 is used as the ion generating device, a case where an ion generating device 2 of Embodiment 2 is used as the ion generating device can also be taken as the example.

As illustrated in FIG. 7, the electrical apparatus 100 has a casing 101 for a fan (hereinafter referred to as a "fan casing 101") part of which is provided with the ion generating device 1, the fan casing 101 constituting an air flow path 102, which is a path through which to guide, to an outside of the ion generating device 1, ions generated by the ion generating device 1.

Thus, in the air flow path 102, the ion generating device 1 and an air sending device 103 for sending gas, by which the ions generated by the ion generating device 1 are carried, are provided. The ion generating device 1 is provided on a downstream side of a direction in which the air sending device 103 sends air. Note that the air sending device 103 can be a sirocco fan, a crossflow fan, or another fan.

The ion generating device 1 can be integrally incorporated into the electrical apparatus 100 or can be provided so as to be detachable and attachable with respect to the electrical apparatus 100. The ion generating device 1 which is provided so as to be detachable and attachable with respect to the electrical apparatus 100 allows the ion generating device 1 to be replaced and cleaned. This facilitates maintenance of the electrical apparatus 100.

The electrical apparatus 100 is not particularly limited in type and can be, for example, an ion generator, an air conditioner, a dehumidification machine, a humidifier, an air cleaner, a fan heater, or another apparatus. The electrical apparatus 100 can be an electrical apparatus for use in a house or an electrical apparatus for automotive use. The electrical apparatus 100 is suitably used to condition air in, for example, a house, a room of a building, a hospital room, a vehicle, an airplane, or a vessel.

As described earlier, a mounting part: 33a can be formed so as to be plate-like. In a case where the mounting part 33a is plate-like, an orientation of a plate surface of the mounting part 33a, which is plate-like, is preferably set in view of an air sending direction in the electrical apparatus 100.

Figure 8:
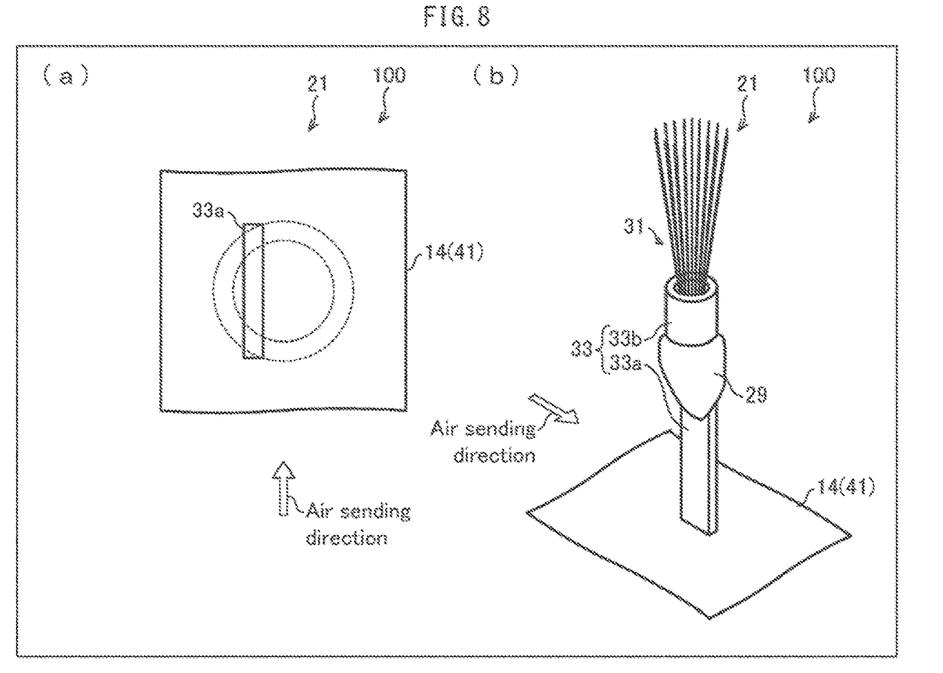
FIG. 8a is a view showing a relationship between (a) an air sending direction in the electrical apparatus in accordance with Embodiment 3 of the present invention.
FIG. 8b is an enlarged perspective view of the discharge electrode in accordance with Embodiment 3 of the present invention.

The following description discusses, with reference to FIG. 8, a relationship between (a) the air sending direction in the electrical apparatus 100 and (b) the orientation of the plate surface of the mounting part 33*a*. (a) of FIG. 8 is a view showing the relationship between (a) the air sending direction in the electrical apparatus 100 and (b) the orientation of the plate surface of the mounting part 33*a*.

(a) of FIG. 8 shows a discharge electrode 21 as an example of a discharge electrode. Note, however, that the following description also applies to a discharge electrode 22. (b) of FIG. 8 is an enlarged perspective view of the discharge electrode 21 and its vicinity of (a) of FIG. 8.

Assume here that in FIG. 8, a direction in which gas by which ions are carried is sent so that the ions are released to an outside of the electrical apparatus 100 is referred to as the air sending direction. As illustrated in FIG. 8, the ion generating device 3 is preferably provided in the electrical apparatus 100 so that the plate surface of the mounting part 33*a* is parallel to the air sending direction.

This is because the plate surface of the mounting part 33*a* which plate surface is parallel to the air sending direction allows a reduction in area of a surface of the mounting part 33*a* which surface is exposed to sent air. The arrangement makes it possible to prevent the mounting part 33*a* from being a hindrance to sending of air. Thus, efficient sending of air can be achieved in the electrical apparatus 100.

The mounting part 33*a*, which is plate-like, can have a greater mechanical strength than a mounting part that is formed in a shape of a pipe whose diameter is small (which is long and narrow). Thus, even the mounting part 33*a* to which an external force is applied is less likely to be deformed (e.g., bent) or be broken.

[Variation]

The description of Embodiment 3 takes, as an example, a case where the electrical apparatus 100 includes the air sending device 103. Note, however, that the air sending device 103 is dispensable. For example, the ions generated by the ion generating device 1 can also be released to the outside of the electrical apparatus 100 by, for example, thermal convection.

[Recap]

An ion generating device (1) in accordance with Aspect 1 of the present invention includes: a discharge electrode (discharge electrode 21, for example) for generating ions by electric discharge, the discharge electrode having (i) a mounting part (mounting part 33*a*, for example) for mounting the discharge electrode on the ion generating device and (ii) a brush part including a plurality of linear electrically conductive members (electrically conductive members 25, for example), and the mounting part binding a base end part of the brush part so as to hold the base end part, the ion generating device further including: a first resin (insulating sealing member 41) with which to seal the base end part of the mounting part; and a second resin (protective resin 29) with which to cover at least a base end surface (brush base end surface 25*t*) of the brush part.

As described earlier, the linear electrically conductive members each have an extremely small outside diameter. In other words, the electrically conductive members are each shaped to be extremely long and narrow. Thus, in a case where a liquid adheres to the base end part of the brush part, in which base end part the plurality of linear electrically conductive members are bound together, a considerable capillary force is generated between the respective electrically conductive members, so that the liquid permeates into an upper part of the brush part by the capillary force.

As described earlier, a resin material (a material of the first resin) may be scattered during formation of the first resin. Such a case may occur in a case where the resin material is vacuum defoamed so that the first resin has a better quality. Then, in a case where the resin material which has adhered to the electrically conductive members cures, the linear electrically conductive members are prevented from spreading. This reduces ion generating capability of the discharge electrode.

Note, however, with the arrangement, a binding part is provided with the second resin with which to cover at least the base end surface of the brush part. Thus, even the resin material which is scattered can be prevented from adhering to the base end surface of the brush part. This allows an ion generating device in accordance with an aspect of the present invention to yield an effect of reducing a risk of performance degradation caused to the ion generating device which is being produced.

In Aspect 2 of the present invention, the ion generating device is preferably arranged such that in Aspect 1 of the present invention, the second resin which has not cured has a viscosity that is higher than a viscosity of the first resin which has not cured.

With the arrangement, the viscosity of the second resin which has not cured is higher than the viscosity of the first resin which has not cured. Thus, it is possible to prevent even the second resin which has not cured from rapidly permeating into the upper part of the brush part by a capillary force. This yields an effect of more reliably preventing a decrease in ion generating capability of the discharge electrode.

In Aspect 3 of the present invention, the ion generating device is preferably arranged such that in Aspect 3 or 2 of the present invention, permeation of the second resin from the base end surface of the brush part is stopped in the base end part of the brush part.

With the arrangement, even in a case where the second resin which has not cured permeates from the base end surface of the brush part, the second resin does not permeate into the upper part of the brush part. This yields an effect of more reliably preventing a decrease in ion generating capability of the discharge electrode.

A method in accordance with Aspect 4 of the present invention for manufacturing an ion generating device in accordance with any one of Aspects 1 through 3 of the present invention preferably includes the steps of: a) providing the discharge electrode with the second resin; b) after the step a), vacuum defoaming a resin material with which to seal the base end part of the mounting part; and c) forming the first resin by causing the resin material which has been vacuum defoamed to cure.

As described earlier, even the resin material which is scattered during the step b) can be prevented from adhering to the base end surface of the brush part. Thus, the arrangement yields an effect of manufacturing an ion generating device without degrading performance of the ion generating device.

An electrical apparatus (100) in accordance with Aspect 5 of the present invention preferably includes: an ion generating device in accordance with any one of Aspects 1 through 3 of the present invention.

The arrangement yields an effect of achieving an electrical apparatus including an ion generating device in accordance with an aspect of the present invention.

In Aspect 6 of the present invention, the electrical apparatus is preferably arranged such that in Aspect 5 of the present invention, the mounting part is plate-like, and the ion generating device is provided so that a plate surface of the mounting part is parallel to an air sending direction, which is a direction in which gas by which ions are carried is sent so that the ions are released to an outside of the electrical apparatus.

The arrangement allows a reduction in area of a surface of the plate-like mounting part which surface is exposed to sent air. Thus, it is possible to prevent the plate-like mounting part from being a hindrance to sending of air. Further, the plate-like mounting part can have a greater mechanical strength than a mounting part that is formed in a shape of a pipe whose diameter is small (which is long and narrow). That is, the arrangement yields an effect of (i) achieving efficient sending of air in the electrical apparatus and (ii) allowing the mounting part to have a greater mechanical strength.

[Additional Remarks]

The present invention is not limited to the embodiments, but can be altered by a skilled person in the art within the scope of the claims. The present invention also encompasses, in its technical scope, any embodiment derived by combining technical means disclosed in differing embodiments. Further, it is possible to form a new technical feature by combining the technical means disclosed in the respective embodiments.

[Another Expression of the Present Invention]

Note that the present invention can also be expressed as below.

Specifically, an ion generating device in accordance with an aspect of the present invention includes: a substrate; a discharge electrode, held by the substrate, for generating ions; a mold resin with which to cover the substrate by causing the discharge electrode to protrude, the discharge electrode including: a plurality of linear electrically conductive members; and a binding part for caulking the plurality of linear electrically conductive members, the plurality of linear electrically conductive members having an end on a mold resin side thereof to which end a resin is applied.

REFERENCE SIGNS LIST

1,2 Ion generating device
21,22 Discharge electrode
25,26 Electrically conductive member
25*t* Brush base end surface (base end surface of brush part)
29 Protective resin (second resin)
33*a*,34*a* Mounting part
41 Insulating sealing member (first resin)
100 Electrical apparatus

The invention claimed is:

1. An ion generating device comprising:
   a discharge electrode for generating ions by electric discharge,
   the discharge electrode having (i) a mounting part for mounting the discharge electrode on the ion generating device and (ii) a brush part including a plurality of linear electrically conductive members, and
   the mounting part binding a base end part of the brush part so as to hold the base end part,
   said ion generating device further comprising:
   a first resin with which to seal the base end part of the mounting part; and
   a second resin with which to cover at least a base end surface of the brush part so as to prevent adhesion of foreign substances to the base end surface of the brush part,
   the second resin being applied to the base end part of the brush part so that the plurality of linear electrically conductive members are bonded with each other and bonded to the mounting part,
   wherein the second resin which has not cured has a viscosity that is higher than a viscosity of the first resin which has not cured.

2. A method for manufacturing an ion generating device recited in claim 1, comprising the steps of:
   a) providing the discharge electrode with the second resin;
   b) after the step a), vacuum defoaming a resin material with which to seal the base end part of the mounting part; and
   c) forming the first resin by causing the resin material which has been vacuum defoamed to cure.

3. An electrical apparatus comprising:
   an ion generating device recited in claim 1.

4. The electrical apparatus as set forth in claim 3, wherein the mounting part is plate-like, and the ion generating device is provided so that a plate surface of the mounting part is parallel to an air sending direction, which is a direction in which gas by which ions are carried is sent so that the ions are released to an outside of the electrical apparatus.

* * * * *